United States Patent [19]

Savu

[11] Patent Number: 4,647,413

[45] Date of Patent: Mar. 3, 1987

[54] PERFLUOROPOLYETHER OLIGOMERS AND POLYMERS

[75] Inventor: Patricia M. Savu, Maplewood, Minn.

[73] Assignee: Minnesota Mining and Manufacturing Company, St. Paul, Minn.

[21] Appl. No.: 572,503

[22] Filed: Jan. 20, 1984

Related U.S. Application Data

[63] Continuation-in-part of Ser. No. 565,226, Dec. 27, 1983, abandoned.

[51] Int. Cl.$^4$ .................... C07C 53/50; C07C 43/11; C08G 59/00

[52] U.S. Cl. .................... 260/544 F; 558/444; 260/544 Y; 558/445; 558/447; 540/596; 562/452; 562/463; 548/950; 562/470; 562/567; 560/45; 562/577; 562/582; 560/53; 564/160; 564/165; 560/60; 564/169; 564/170; 560/111; 548/962; 564/194; 560/170; 564/199; 564/200; 560/174; 564/201; 564/202; 560/180; 568/308; 568/336; 560/184; 568/413; 568/416; 560/223; 568/607; 568/615; 560/264; 560/356; 528/402; 204/159.13; 560/356; 204/159.16; 528/402; 544/182; 544/216; 546/262; 546/275; 546/281; 546/314; 548/406; 548/518; 548/565; 548/571; 556/413; 556/414; 556/416; 556/417; 556/419; 558/389; 558/440; 558/441; 564/193

[58] Field of Search .................... 548/406, 518, 565, 571; 260/544 F, 544 Y, 239 A, 239 B; 204/159.11; 568/615, 308, 336, 413, 416, 607; 560/180, 45, 63, 60, 111, 170, 174, 184, 223, 264, 356; 564/160, 165, 169, 170, 193, 194, 199, 200, 201, 202; 562/452, 463, 470, 567, 577, 582; 558/389, 440, 441, 444, 445, 447; 556/413, 414, 416, 417, 419; 544/182, 216; 546/262, 275, 281, 314

[56] References Cited

U.S. PATENT DOCUMENTS

| | | | |
|---|---|---|---|
| 2,717,871 | 9/1955 | Scholberg et al. | 204/59 |
| 3,125,599 | 3/1964 | Warnell | 260/535 |
| 3,250,807 | 5/1966 | Fritz et al. | 260/535 |
| 3,250,808 | 5/1966 | Moore et al. | 260/535 |
| 3,392,097 | 7/1968 | Gozzo et al. | 204/159.22 |
| 3,442,942 | 5/1969 | Sianesi et al. | 260/544 |
| 3,505,411 | 4/1970 | Rice | 260/615 |
| 3,637,842 | 1/1972 | Stump et al. | 260/544 F |
| 3,660,315 | 5/1972 | Hill et al. | 260/544 F |
| 3,699,145 | 10/1972 | Sianesi et al. | 260/463 |
| 3,715,378 | 2/1973 | Sianesi et al. | 260/463 |
| 3,810,875 | 5/1974 | Rice et al. | 260/899 |
| 3,845,051 | 10/1974 | Zollinger | 260/248 CS |
| 3,849,504 | 11/1974 | Mitsch | 260/615 BF |
| 3,950,588 | 4/1976 | McDougal | 428/288 |
| 3,972,856 | 8/1976 | Mitsch et al. | 260/77.5 AP |
| 4,094,911 | 6/1978 | Mitsch et al. | 260/615 A |
| 4,239,828 | 12/1980 | Knope et al. | 428/64 |

OTHER PUBLICATIONS

*Hackh's Chemical Dictionary* 4th Ed. (1969) McGraw-Hill Publ. p. 203.

*College Dictionary* (1973) Random House, Publ. at p. 692.

G. Caporiccio et al., Ind. Eng. Chem. Prod. Res. Dev. 1982, 21, 515-519.

J. F. Harris, Jr., J. Org. Chem. 30, 2182 (1965).

R. A. Mitsch, J. Org. Chem. 35, 2816 (1970).

*Primary Examiner*—Natalie Trousof
*Assistant Examiner*—L. Hendriksen
*Attorney, Agent, or Firm*—Donald M. Sell; James A. Smith; William G. Ewert

[57] ABSTRACT

Perfluoropolyether oligomers or block polymers, having a backbone with one or a plurality of perfluoropolyether segments each consisting essentially of (1) at least one perfluoroisopropyleneoxy unit, (2) a bis(perfluoromethyleneoxy-terminated) unit, and (3) a perfluoroethylidene unit terminating each segment, the backbone of the perfluoropolyether being terminated with COF and/or a functional or nonfunctional derivative thereof, said perfluoropolyethers being made by reacting a perfluoroaliphatic diacid fluoride with hexafluoropropylene epoxide to produce an acid fluoride-terminated perfluoropolyether adduct or oligomer which then can be photopolymerized to yield an acid fluoride-terminated perfluoropolyether block polymer. These oligomers and block polymers are useful as high temperature lubricants, hydraulic fluids, gaskets, adhesives and coatings as well as co-reactants wtih urethane in forming propellant binders.

8 Claims, No Drawings

PERFLUOROPOLYETHER OLIGOMERS AND POLYMERS

This application is a continuation in part of copending application Ser. No. 565,226, filed Dec. 27, 1983, now abandoned.

This invention relates to perfluoropolyether oligomers and polymers. In another aspect, it relates to a process for the preparation of such materials from hexafluoropropylene epoxide and diacid fluorides. In another aspect, it relates to difunctional perfluoropolyether polymers and a photopolymerization process for the preparation thereof. In a still further aspect, it relates to poly(perfluoroalkyleneoxy) polymers terminated with acid fluoride groups and derivatives thereof.

Perfluoropolyethers, though developed over the last two decades or so, are still considered a relatively new class of chemical substances. (Sometimes they are named in the art as poly(perfluoroalkylene oxides), poly(perfluoroalkyleneoxy) substances, or fluorocarbon ethers). They usually have one or two types of repeating perfluoroalkyleneoxy units that form a backbone or linear chain of catenary carbon and oxygen atoms, which chain in the case of compounds or oligomers is terminated with functional and/or nonfunctional groups. Generally, the perfluoropolyethers have relatively high temperature and chemical resistance, nonflammability, low glass transition temperatures, oil and water repellency, anti-corrosivity, and have surfactant, lubricating, and high dielectric strength characteristics, useful properties which have stimulated much development or application activity.

Several general types of perfluoropolyethers have been described in the literature. The earliest type is characterized by one or several homopolymeric segments or blocks of repeating units of the formula —CF(CF$_3$)CF$_2$O— and made from hexafluoropropylene epoxide, e.g., see U.S. Pat. No. 3,250,807. Another type is that characterized by blocks of repeating units of the formula —CF$_2$CF$_2$O— and made from tetrafluoroethylene epoxide, e.g., see U.S. Pat. No. 3,125,599. Others, made by reacting oxygen with tetrafluoroethylene or hexafluoropropylene, are characterized by a backbone made of repeating —CF$_2$O— units, e.g., see U.S. Pat. No. 3,392,097, or —CF(CF$_3$)CF$_2$O— units, e.g., see U.S. Pat. No. 3,442,942, or, in addition to either of these units, units of the formula —CF(CF$_3$)O—, e.g., see U.S. Pat. No. 3,699,145, or a backbone consisting of randomly distributed —CF$_2$O— and —CF$_2$CF$_2$O— units, e.g., see U.S. Pat. No. 3,715,378, or a backbone made up of —CF(CF$_3$)CF$_2$O— and —CF$_2$CF$_2$O— units and, optionally, —CF$_2$O— and —CF(CF$_3$)O— units. Another type of perfluoropolyether is that characterized by backbone units of the formula —(CF$_2$)$_a$O(CF$_2$)$_b$— made by photopolymerization, e.g., see U.S. Pat. No. 3,505,411 (Rice) and 3,849,504 (Mitsch et al).

The backbones of these prior art perfluoropolyethers are variously terminated with functional groups, e.g., —COF, or nonfunctional (inert) moieties, e.g., —CF$_3$. Various patents disclose a host of functional derivatives of the perfluoropolyethers, e.g., see U.S. Pat. No. 4,094,911 (Mitsch et al) which discloses perfluoropolyethers terminated with polymerizable functional groups. U.S. Pat. No. 3,810,875 (Rice et al) discloses use of perfluoropolyethers with ethylenically unsaturated monomers in making block copolymers. Perfluoropolyethers with nonfunctional terminal moieties are sold under the trademarks "KRYTOX" and "FOMBLIN" for use as vacuum pump fluids, e.g., see G. Caporiccio et al, Ind. Eng. Chem. Prod. Res. Dev. 1982, 21, 515–519.

Of particular relevance to the instant invention is U.S. Pat. No. 3,637,842 (Stump et al), which discloses the preparation of perfluoropolyether polymers of the formula X[CF(CF$_3$)O (CF$_2$)$_p$OCF(CF$_3$)]$_n$X where X is —COF or —CH$_2$OH, p is 2 to 23, and n is 2 to 12, by the photopolymerization of a starting ether wherein subscript n in the foregoing formula is 1 and X is —COF, the starting ether being prepared by the reaction of diacid fluorides with hexafluoropropylene epoxide as described in said U.S. Pat. No. 3,250,807. These polymers, containing a central bis(perfluoroalkyleneoxy) unit and a perfluoroethylidene unit on each side thereof, have a carbon-to-oxygen ratio of limited variability.

Briefly, this invention provides in one aspect perfluoropolyether substances comprising one or a mixture of chemical compounds which are linear oligomers or block polymers with a backbone consisting or consisting essentially of one or a plurality of perfluoropolyether segments or blocks, each of which consists of three different divalent units, namely, (1) at least one perfluoroisopropyleneoxy unit, the number of which in each segment being the same or different, (2) a bis(perfluoromethyleneoxy-terminated) unit, and (3) two perfluoroethylidene units, said (1) and (2) units being bonded together within the segment or block in the form of a chain each end of which is terminated with or bonded to one of said perfluoroethylidene units, the backbone of the perfluoropolyether being terminated with or bonded to COF and/or a one- or multi-step derivative thereof which can be functional, e.g. COOCH$_3$, or nonfunctional, e.g. CF$_3$.

A class of said perfluoropolyethers can be represented by the formula

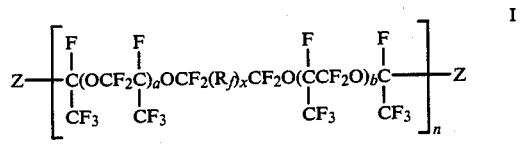

where
 each Z is independently a functional moiety, such as COF or a derivative thereof, such as one containing a polymerizable group, or a nonfunctional (or inert) moiety, such as CF$_3$, F, Cl, or H,
 n is an integer or number greater than 1, e.g. 2 to 20, and preferably 2 or 4,
 a and b are independently (which can be zero) an integer or number up to about 10, with the proviso that the sum of a+b is equal to at least 1 and can be as high as 35 or higher,
 x is zero or 1, and
 R$_f$ is a fluoroaliphatic group, e.g. perfluoroalkylene, which can contain one or a plurality, e.g. 2 to 4, of hetero atoms, such as catenary oxygen or nitrogen atoms, e.g. oxybis(perfluoroalkylene), said fluoroaliphatic groups having, for example, 1 to 21 carbon atoms, preferably 1 to 4 catenary carbon atoms (particularly where R$_f$ is perfluoroalkylene).

A preferred subclass of the oligomers or polymers are those represented by the formula I where Z is selected from the group consisting of H, X, CF$_2$H, CF$_2$X, CH$_2$OH, COX, COR, COOH, COOM, COOR, CF$_2$R, CH$_2$OC(O)CR'=CH$_2$, CON(R")R", CH$_2$NH$_2$, CH$_2$NCO, CN, C$_3$N$_3$(R$_f$)$_2$, CH$_2$OCOR, where X is F, Cl, or Br, M is an ammonium radical or a monovalent metal atom, R is alkyl, e.g. with 1–8 carbon atoms, aryl, e.g. with 6, 10, or 12 ring carbon atoms, or a combination thereof, i.e. alkylaryl or arylalkyl, R' is H or CH$_3$, R" is H or said R, (CH$_2$)$_z$Si(R''')$_3$, where z is an integer of 2 to 11 and R''' is a hydrolyzable group such as methoxy, or the two R" groups in CON(R")R" can together form an alkylene moiety, e.g. with 2 to 6 carbon atoms, which together with the amido nitrogen atom form a heterocyclic ring, e.g. NC$_6$H$_{10}$, and R$_f$ is as defined above except it is monovalent.

For brevity, the portion of the above-described perfluoropolyethers, excluding the terminal groups, Z, will occasionally hereafter be referred to as the perfluoropolyether chain or "PPE".

The perfluoropolyether polymers of this invention can be prepared by two steps: (1) the condensation or addition reaction of a perfluoroaliphatic diacid (or diacyl) fluoride, FOC(R$_f$)$_x$COF, with hexafluoropropylene epoxide (HFPO) to produce an acid fluoride-terminated adduct or oligomer product (having a structure like that of formula I where Z is COF but n is 1 and a+b need not be greater than 1), followed by (2) the ultraviolet light-induced cleavage/coupling reaction or photopolymerization of the acid fluoride-terminated adduct to yield the acid fluoride-terminated coupled product or block polymer (having the structure of formula I above where Z is COF and n is greater than 1). The photopolymer product can be further reacted by known techniques to yield one- or multi-step derivatives having a large variety of end groups, Z, which may be functional or nonfunctional and whose structures are also encompassed by formula I. The oligomer product of the first step and the photopolymer of the second step generally are mixtures of perfluoropolyethers and some impurities and byproducts. They can be purified or resolved by distillation or chemical means.

The condensation of perfluoroaliphatic acid fluorides with HFPO generally can be carried out as described in U.S. Pat. No. 3,250,807 (Fritz et al). For example, it can be carried out in an aprotic solvent (e.g. diglyme) in a molar ratio of HFPO to diacid fluoride of at least 3:1 and in the presence of anhydrous alkali metal fluoride catalyst (e.g. KF). The resulting acid fluoride adduct product comprises or consists essentially of a mixture of difunctional oligomers, e.g. 90 to 95 wt. % or more and usually contain a small amount, e.g. up to 5 to 10 wt. % of impurities, typically monofunctional acid fluorides, which can be removed by distillation to provide perfluoropolyethers which consist or consist essentially of the above described oligomers.

The UV-catalyzed coupling reaction of the resulting acid fluoride adduct product can be carried out as described by J. F. Harris, Jr. in J. Org. Chem. 30, 2182 (1965) or by R. A. Mitsch in J. Org. Chem. 35, 2816 (1970) and U.S. Pat. No. 3,849,504. The resulting photopolymer product comprises or consists essentially of a mixture of perfluoropolyethers which are diacid fluorides, and a minor amount, e.g. 5 weight % or less, of byproducts, and such product can also be resolved into polyether fractions or purified, and derivatives can be prepared from the acid fluorides.

The various acid fluoride derivatives of this invention (the terminal or end groups of which are encompassed by Z in formula I) can be made by known derivative techniques, such as described in said U.S. Pat. Nos. 3,250,807 (Fritz et al.) and 4,094,911 (Mitsch et al). The di(methylcarboxylate), i.e., the polymers of forumla I where Z is COOCH$_3$, is particularly useful as an intermediate in the preparation of a host of derivatives useful in a variety of applications, such as described in said U.S. Pat. No. 4,094,911.

In preparing the perfluoropolyether of this invention, it has been found particularly useful to photolyze the distilled acid fluoride-terminated HFPO adducts (dissolved in an inert fluorocarbon solvent) using a 450-watt medium pressure mercury lamp located inside a water-cooled quartz sleeve, the lamp-sleeve assembly being immersed in the fluorocarbon solvent-HFPO adduct solution. Irradiation can be carried out in a satisfactory manner at 25° to 40° C. (ambient conditions, no external cooling or warming) for varying times, e.g. 3 to 15 hours. The extent of chain coupling (polymerization) can be monitored by withdrawing small samples of the fluorocarbon solution and measuring changes in viscosity. The perfluoropolyether polymer products can be isolated, for example by distillation or vacuum stripping of low boiling materials. Molecular weight of the products can be determined by end group analysis utilizing F-nmr and acid-base titration.

Said U.S. Pat. No. 4,094,911 describes techniques for the preparations of a host of COF-derived derivatives of another class of perfluoropolyethers and U.S. Pat. No. 3,950,588 (McDougal) describes a technique for preparing perfluoropolyethers with —CONH(CH$_2$)$_z$Si(R''')$_3$ end groups, where R''' is halo, alkoxy, or acyloxy, such as —CONH(CH$_2$)$_3$Si(OCH$_3$)$_3$ end groups. The said techniques of the above-described references are hereby incorporated by reference in the interest of brevity.

An illustrative overall outline for the synthesis of perfluoropolyethers of this invention from HFPO and perfluorosuccinyl fluoride is as follows where a+b is at least 1:

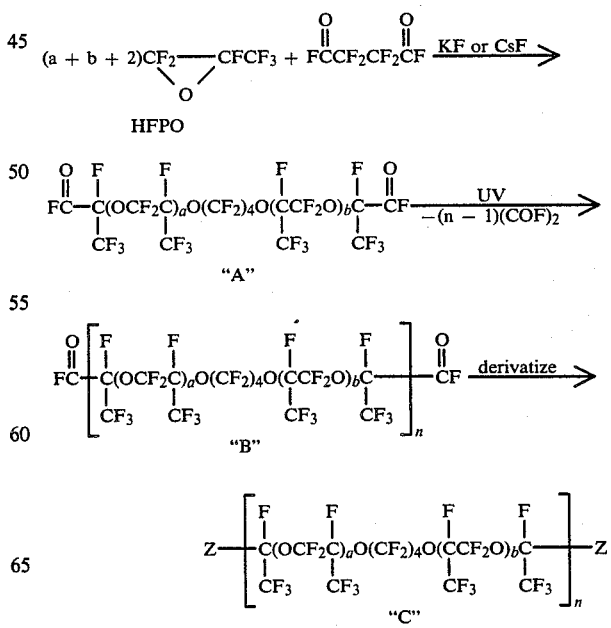

Representative reactions for the preparations of said perfluoropolyether derivatives of this invention are shown in Schemes 1-20.

1. FOC—"PPE"—COF + ROH ⟶ ROOC—"PPE"—COOR

2. FOC—"PPE"—COF + HN(R″)R″ ⟶
   R″(R″)NOC—"PPE"—CON(R″)R″

3. FOC—"PPE"—COF $\xrightarrow{(H)}$ HOCH$_2$—"PPE"—CH$_2$OH

4. FOC—"PPE"—COF $\xrightarrow{KOH, HO(CH_2)_2OH}$ H—"PPE"—H

5. H—"PPE"—H $\xrightarrow{\Delta, X_2}$ X—"PPE"—X

6. HOCH$_2$—"PPE"—CH$_2$OH + CH$_2$=CR″COCl ⟶
   CH$_2$=CR″OCOCH$_2$—"PPE"—CH$_2$OCOCR″=CH$_2$

7. FOC—"PPE"—COF + H$_2$O ⟶ HO$_2$C—"PPE"—CO$_2$H

8. HO$_2$C—"PPE"—CO$_2$H + 2/pM(OH)$_p$ ⟶
   M$_{1/p}$O$_2$C—"PPE"—CO$_2$M$_{1/p}$

9. HOCH$_2$—"PPE"—CH$_2$OH + NaOR ⟶
   ROCH$_2$—"PPE"—CH$_2$OR

10. HOCH$_2$—"PPE"—CH$_2$OH + RCOX ⟶
    ROCOCH$_2$—"PPE"—CH$_2$OCOR

11. NH$_2$CO—"PPE"—CONH$_2$ + P$_2$O$_5$ ⟶ NC—"PPE"—CN

12. NC—"PPE"—CN $\xrightarrow[cat., \Delta]{4R_fCN}$

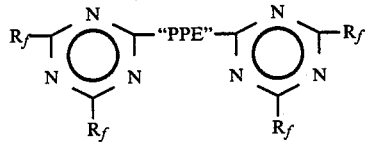

13. H$_2$NCO—"PPE"—CONH$_2$ $\xrightarrow{LiAlH_4}$
    NH$_2$CH$_2$—"PPE"—CH$_2$NH$_2$ 14. NH$_2$CH$_2$—"PPE"—CH$_2$NH$_2$ $\xrightarrow{COCl_2 \; CaO}$
    OCNCH$_2$—"PPE"—CH$_2$NCO 15. FOC—"PPE"—COF $\xrightarrow{AlCl_3 \; RH}$ ROC—"PPE"—COR 16. RCO—"PPE"—COR $\xrightarrow{SF_4}$ RCF$_2$—"PPE"—CF$_2$R 17. RO$_2$C—"PPE"—CO$_2$R $\xrightarrow{SF_4}$ ROCF$_2$—"PPE"—CF$_2$OR 18. FOC—"PPE"—COF $\xrightarrow{SF_4}$ CF$_3$—"PPE"—CF$_3$ 19. RO$_2$C—"PPE"—CO$_2$R + NH$_2$(CH$_2$)$_3$Si(OCH$_3$)$_3$ ⟶
    (CH$_3$O)$_3$Si(CH$_2$)$_3$NHCO—"PPE"—CONH(CH$_2$)$_3$Si(OCH$_3$)$_3$ 20. HOCH$_2$—"PPE"—CH$_2$OH $\xrightarrow{NaOH, ClCH_2CH_2CH\overset{O}{\overset{|}{\diagup}}}$

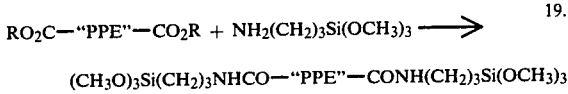

Representative diacid fluoride compounds, FOC—(R$_f$)$_x$—COF, suitable for reaction with HFPO include perfluoroalkanoic diacid fluorides such as oxalyl fluoride, difluoromalonyl fluoride, tetrafluorosuccinyl fluoride, hexafluoroglutaryl fluoride, octafluoroadipyl fluoride, 1,4-bis(fluorocarbonyl)perfluorocyclohexane, oxybis(difluoroacetyl fluoride), oxybis(tetrafluoropropionyl fluoride), bis(2-fluorocarbonyltetrafluoroethyl)-trifluoromethyl amine, and perfluorosebacyl fluoride. These diacid fluorides can be conveniently prepared by the known electrochemical fluorination process, in which the appropriate hydrocarbon precursor is dissolved in liquid hydrogen fluoride and subjected to electrochemical fluorination following the procedures described, for example, in U.S. Pat. No. 2,717,871 (Scholberg et al). The crude acid fluoride product is generally treated with sodium fluoride, filtered, and distilled.

Particularly useful perfluoropolyether adduct or oligomer products of this invention are those having a number average molecular weight range of about 542, where (R$_f$)$_x$ is —CF$_2$OCF$_2$—, to 1200, preferably about 800 to 900. The perfluoropolyether polymer products can have number average molecular weights of about 990 to 12,000, preferably 2000 to 3000. Such products are normally liquids of relatively low viscosity and low vapor pressure (low volatility). In particular, the non-functional or inert oligomer products, where Z is H, F, Cl, or an R$_f$-substituted triazine ring as shown in the product of Scheme 12, supra, having a number average molecular weight in the range of 2000 to 3500, have good viscosity-temperature properties, are nonflammable, thermally stable, and resistant to oxidation, properties which make them particularly useful as high performance fluids for use in high temperature and/or oxidizing environments, e.g. as lubricants, pump fluids, hydraulic fluids, and heat transfer fluids, such as described in U.S. Pat. No. 3,845,051 (Zollinger).

The inert oligomers can also be used as lubricants for magnetic media, for example, like the polyethers in U.S. Pat. No. 4,239,828 (Knope et al).

The functional perfluoropolyethers of this invention can be used in a host of applications, for example, the same applications disclosed in the prior art for the related, similarly functional, perfluoropolyethers having a backbone made up of —CF$_2$O(CF$_2$CF$_2$O)$_m$(CF$_2$O)$_n$CF$_2$—.

For example, the perfluoropolyethers of this invention terminated with reactive radicals which are or contain a polymerizable group can be used as monomers in the preparation of polymeric materials, such as polyurethanes (useful as a propellant binder) formed by reacting the methylol-terminated perfluoropolyethers with polyisocyanates as described in U.S. Pat. Nos. 3,972,856 (Mitsch et al) and 4,094,911 (Mitsch et al).

The acid and hydroxyl functional polyethers of this invention can also be used to form bladders, seals, O-rings, gaskets, adhesives, coatings, etc., as described in U.S. Pat. No. 3,637,842. Those terminated with silyl groups, such as the product of Scheme 19, supra, can be used in the treatment of substrates or articles having silanol-reactive surfaces, such as described in U.S. Pat. No. 3,950,588 (McDougal). Other applications are those described in U.S. Pat. Nos. 3,810,875 (Rice et al), 3,637,842 (Stump), and 3,250,807 (Fritz et al).

Objects and advantages of this invention are illustrated in the following examples, which should not be construed to unduly limit the invention.

EXAMPLE 1

Thirty ml bis(2-methoxyethyl) ether ("diglyme"), which was dried by distillation from sodium, was placed in a dry flask fitted with a dry ice-cooled condenser, mechanical stirrer, gas inlet tube, and thermometer. Potassium fluoride (1.2 g), which was dried in a vacuum oven for 6 hrs. at 150° C., was weighed under a dry nitrogen atmosphere and transferred into the flask under a nitrogen stream. Tetrafluorosuccinyl fluoride (23.5 g) was condensed in a dry ice-cooled trap ($-78°$ C.) and transferred into the reaction flask via rubber tubing connected to the gas inlet tube by inverting the trap. The reaction mixture was stirred at ambient temperature for 30 min. and the flask was cooled in a $-22°$ C. bath (dry ice/CCl$_4$) and 62 g HFPO was added over a 2-hour period at such a rate that inlet and outlet pressures were balanced. Stirring under a dry nitrogen atmosphere at $-22°$ C. was continued for 1 hr. and the cooling bath was removed. The reaction mixture was then stirred at ambient conditions for an additional hour and allowed to stand overnight at room temperature. Sixty ml of "Freon" 113 was added and the mixture stirred for 5 min. and poured into a separatory funnel. The phases were allowed to separate, and the lower phase, comprising crude HFPO/succinyl fluoride adduct product, was distilled at atmospheric pressure. Boiling ranges of the fractions (or cuts) obtained are shown in Table 1.

TABLE 1

Boiling Ranges of HFPO—Succinyl Fluoride Adduct Fractions

| Fraction no. | Head temp. (°C.) | Pot temp. (°C.) | Weight (g) |
|---|---|---|---|
| 1 | 45–47 | 100–163 | (Freon 113) |
| 2 | 85–120 | 160–175 | 5.3 |
| 3 | 120–160 | 175–198 | 13.4 |
| 4 | 160–170 | 195–198 | 11.5 |
| 5 | 170–203 | 198–260 | 32.4 |

Gas-liquid chromatographic (GLC) and fluorine nuclear magnetic reasonance (F-nmr) analysis of the distilled liquid products support the structure of the adduct product as represented by formula I supra where $(R_f)_x$ is —CF$_2$CF$_2$—, Z is —COF, and n is 1. HFPO:succinyl fluoride ratios of the distilled products are given in Table 2.

TABLE 2

| Fraction no. | Composition of the Distillation Fractions Ratio of HFPO:succinyl fluoride (GLC area, %) | | | | |
|---|---|---|---|---|---|
| | 1:1 | 2:1 | 3:1 | 4:1 | 5:1 |
| 2 | 35.1 | 37.6 | 12.2 | 1.8 | — |
| 3 | 8.4 | 43.2 | 39.8 | 7.3 | — |

TABLE 2-continued

| Fraction no. | Composition of the Distillation Fractions Ratio of HFPO:succinyl fluoride (GLC area, %) | | | | |
|---|---|---|---|---|---|
| | 1:1 | 2:1 | 3:1 | 4:1 | 5:1 |
| 4 | — | 17.7 | 67.4 | 14.1 | — |
| 5 | — | — | 44.6 | 42.2 | 6.8 |

The overall yield of adduct based on diacid fluoride (80% tetrafluorosuccinyl fluoride) was 81%.

A 60.2 g mixture of HFPO-tetrafluorosuccinyl fluoride adduct fractions prepared as described above, and consisting of 12 wt. % of the 2:1 adduct, 26 wt. % of the 3:1 adduct, 41 wt. % of the 4:1 adduct, and 17 wt. % of the 5:1 adduct, was dissolved in 340 g dry "FC-75" fluorocarbon solvent and placed in an immersion type photoreactor under a dry nitrogen atmosphere. The solution was irradiated with a 450-watt medium pressure mercury ultraviolet lamp for 4.75 hrs. The viscosity of the reaction solution was monitored about every hour. The viscosity increased from an initial value of 1.08 cs at 23° C. to 1.30 cs at 23° C. when the reaction was stopped. The reaction mixture containing the perfluoropolyether photopolymer of this invention having structure depicted in formula I, where $(R_f)_x$ is —CF$_2$CF$_2$— and Z is COF was distilled through a Vigreux column at atmospheric pressure. The boiling ranges and product identity of the photopolymer fractions are shown in Table 3.

TABLE 3

Distillation, Boiling Ranges, and Identities of Fractions

| Fraction no. | Distillation pressure | Boiling range °C. | Weight (g) | Identity |
|---|---|---|---|---|
| 1 | atmospheric | 95–110 | — | FC-75 |
| 2 | atmospheric | 155–210 | 12.6 | HFPO—diacid fluoride adduct[a] |
| 3 | 0.2 torr | 115–135 | 0.8 | photopolymer[b] |
| 4 | 0.2 torr | 135–305 | 28.2 | photopolymer[b] |
| 5 | — | — | 6.1 | photopolymer[b] (pot residue) |

[a]This adduct had a structure like formula I where Z is COF and n is 1.
[b]This photopolymer had a structure like formula I where $(R_f)_x$ is —CF$_2$CF$_2$— and Z is COF.

EXAMPLE 2

Following the procedure of Example 1, 43.5 g oxybis(difluoroacetyl fluoride) was dissolved in 60 ml diglyme containing 1.00 g dry potassium fluoride. To this stirred misture was added 122.7 g HFPO and the reaction mixture allowed to stir overnight with gradual warming to room temperature. The lower phase (96.1 g) of the reaction mixture, comprising crude HFPO-oxybis(difluoroacetyl fluoride) adduct, was distilled through a Vigreux column at atmospheric pressure. Boiling ranges are shown in Table 4.

TABLE 4

Boiling Ranges of HFPO—Oxybis(difluoroacetyl Fluoride) Adduct Fractions

| Fraction no. | Head temp. (°C.) | Pot temp. (°C.) | Weight (g) |
|---|---|---|---|
| 1 | 65–75 | 105–130 | 22.1 |
| 2 | 75–100 | 130–135 | 4.1 |
| 3 | 100–135 | 135–160 | 26.5 |
| 4 | 135–137 | 160–183 | 17.0 |
| 5 | 137–161 | 183–235 | 16.0 |
| 6 | 161–167 | 235–300 | 2.2 |

Fractions 3 through 5 were combined and analyzed by F-nmr. The analytical results supported the structure of the combined adduct fractions as one like that designated "A" in the overall synthesis outline supra except that the central unit was —O(CF$_2$)$_2$O(CF$_2$)$_2$O—. A 42.2 g mixture of distilled HFPO-oxybis(difluoroacetyl fluoride) adducts, prepared as described in Example 2, was dissolved in 400 g FC-75 solvent and irradiated for 13 hrs. using the apparatus and procedure of Example 1. The FC-75 solvent was distilled at atmospheric pressure and remaining material distilled at 0.1 torr. Two fractions were obtained, the first (19 g) boiling at 25°–160° C., and the second (18.9 g) boiling at 160°–260° C. F-nmr analysis of the second fraction was consistent with a structure like that of formula I, where (R$_f$)$_x$ is —CF$_2$OCF$_2$— and Z is COF.

EXAMPLE 3

A 56.1 g mixture of HFPO-tetrafluorosuccinyl fluoride adducts having the same composition as described in Example 3 was dissolved in 316 g of FC-75 fluorocarbon solvent and irradiated for 4.5 hrs. using the apparatus and procedure of Example 3. The viscosity of the reaction solution at 23° C. was 1.37 cs. Distillation gave 4 g unreacted adducts boiling at 110°–135° C. and three fractions of photopolymer, viz., 1., 5.3 g boiling at 55°–135° C. at 0.2 torr, 2., 26.2 g boiling at 155°–300° C. at 0.2 torr, and 3., 12.6 g pot residue.

The structure and molecular weight of the above three perfluoropolyether photopolymer fractions as determined by F-nmr are presented in Table 5.

—OCFHCF$_3$ (major), —OCF$_2$CF$_2$CF$_2$H, —OCF$_2$CF$_2$CF$_3$, and —OCF(CF$_3$)CF$_2$H.

EXAMPLE 5

This example describes the conversion of hydride-terminated, perfluoropolyether photopolymer to chloride-terminated polymer. Hydride-terminated polymer (19.9 g), prepared as in Example 4, was placed in a flask and heated to 200° C., then chlorine gas was bubbled into the liquid polymer over a 6-hour period while the heating was continued. (An H-nmr analysis run after 4 hrs. of chlorination indicated that only about 10 wt. % of the terminal hydrogen atoms were still present.) At the end of the 6-hour chlorination, the reaction mixture was allowed to cool and excess chlorine was removed under reduced pressure employing a water aspirator. A total of 18.2 g of perfluoropolyether product was obtained. F-nmr indicated the presence of only the following end groups: —OCF(Cl)CF$_3$ (major), —OCF$_2$CF$_2$CF$_2$Cl, OCF(CF$_3$)CF$_2$Cl, —OCF$_2$Cl, and —OCF$_2$CF$_2$CF$_3$.

EXAMPLE 6

This example describes the direct preparation of chloride-terminated perfluoropolyether photopolymer from acid fluoride-terminated polymer having the structure of formula I where (R$_f$)$_x$ is CF$_2$CF$_2$ and Z is COF. Photopolymer (104.6 g of fractions with the following boiling ranges: less than 155° C. at 1.5 torr (9 g), 155°–310° C. at 1.5 torr (67.6 g), above 310° C. at 0.15 torr (28 g)) was dissolved in 190 g FC-70 fluorocarbon

TABLE 5

| | | Mole % by F-nmr | | | | | |
|---|---|---|---|---|---|---|---|
| | | Internal units | | | End groups | | |
| Fraction no. | No. ave. mol. wt. | —OCF$_2$CFO—<br>\|<br>CF$_3$ | —OCF—CFO—*<br>\| \|<br>CF$_3$ CF$_3$ | —O(CF$_2$)$_4$O— | —OCFCOF<br>\|<br>CF$_3$ | —OCF$_2$CF$_2$CF$_3$ | —OCF$_2$CF$_2$CF$_2$COF |
| 1 | 1094 | 45.8 | 3.8 | 17.8 | 28.1 | 3.7 | 0.8 |
| 2 | 3249 | 51.1 | 15.9 | 21.6 | 9.2 | 1.6 | 0.5 |
| 3 | 6316 | 52.2 | 18.2 | 23.7 | 4.9 | 1.0 | — |

*This unit is a bis(perfluoroethylidene) made up of two terminal perfluoroethylidene units of vicinal polyether segments.

EXAMPLE 4

The following example describes the conversion of the acid fluoride end groups of perfluoropolyether photopolymers of this invention to hydride end groups.

Perfluoropolyether photopolymer (14.9 g) prepared as described in Example 1 was placed in a flask fitted with a thermometer, Vigreux column, and distillation head. Fifteen ml ethylene glycol and 15 ml 2.5 molar KOH solution (aqueous) were added to the reaction flask and the reaction mixture heated to 140° C. Vigorous foaming took place and water distilled out of the reaction mixture via the distillation head. When no further foaming was observed and all the water had distilled out of the flask, the pot temperature was gradually increased until it reached 200° C. Heating was continued for an additional 2 hrs., then 50 ml FC-75 and 150 ml water were added. The reaction mixture was agitated and the lower phase was separated and dried over silica gel. Removal of the FC-75 solvent at reduced pressure gave 11.4 g residual liquid product. Infrared analysis indicated the complete absence of any carbonyl absorption. Distillation at 0.2 torr gave a fraction (76 wt. % of the total) boiling at 145°–287° C., which was analyzed by F-nmr and H-nmr. The following end groups were found for the perfluoropolyether fraction:

solvent and placed in a flask fitted with a thermometer, mechanical stirrer, condenser, and gas inlet tube. Sodium carbonate (22 g) was added and stirring and heating was begun. Gas evolution started at 43° C. and at 90° C. rapid gas evolution was taking place. After 0.5 hr. at 90° C., the addition of chlorine gas was started and the temperature was raised to 190° C. Chlorine addition to the heated, stirred reaction mixture was continued for 5.5 hrs. until 116 g of chlorine had been added. The reaction mixture was allowed to cool, 200 ml of Freon 113 was added, the reaction mixture was filtered, and solvents were removed by distillation. The residual liquid product weighed 85.3 g. An additional 4.5 g of product was obtained by washing the filtered solids with fluorocarbon solvent and evaporating the solvent. Vacuum distillation (0.15 torr) of the combined crude product gave the following fractions: No. 1. 110°–155° C. (10.3 g), No 2. 155°–312° C. (67.6 g), No. 3. pot residue (9 g). F-nmr of fraction No. 2 gave the results shown in Table 6.

TABLE 6

| | Contribution to the polymer, mole % |
|---|---|
| Internal Units | |

TABLE 6-continued

| | Contribution to the polymer, mole % |
|---|---|
| —OCF$_2$CF(CF$_3$)O— | 43.8 |
| —O(CF$_2$)$_4$O— | 22.6 |
| —OCF(CF$_3$)CF(CF$_3$)O— | 17.9 |
| —O(CF$_2$)$_6$O— | 1.9 |
| End Groups | |
| —OCF(Cl)CF$_3$ | 5.2 |
| —O(CF$_2$)$_3$Cl, —O(CF$_2$)$_4$Cl, and —CF(CF$_3$)CF$_2$Cl | 3.0 |
| —OCF(Cl)CF$_2$Cl | 1.9 |
| —OCFHCF$_3$ | 2.0 |
| —OCF$_2$CF$_2$CF$_3$ | 0.8 |
| —OCF(CF$_3$)COF | 0.7 |
| —CF(CF$_3$)$_2$ | 0.3 |

End group analysis (from the above F-nmr data) indicated a molecular weight for the perfluoropolyether of 2657.

EXAMPLE 7

The viscosity-temperature properties of the hydrogen- and chlorine-terminated perfluoropolyether photopolymers of the invention were measured and compared with a chlorine-terminated perfluoropolyether polymer of known backbone structure and a commercial perfluoropolyether non-functional fluid. The results are presented in Table 7.

TABLE 7

Viscosity-Temperature Relationships of Perfluoropolyether Fluids

| Perfluoropolyether | Boiling range at 0.1 torr (°C.) | Number average mol. wt.[e] | Viscosity (centistokes) | | |
|---|---|---|---|---|---|
| | | | 24° C. | 40° C. | 55° C. |
| 1[a] | 160–305 | 2406 | 330 | 104 | 45 |
| 2[b] | 150–360 | 3400 | 240 | 85 | 45 |
| 3[b] | 160–310 | 2900 | 163 | 70 | 39 |
| 4[c] | 155–312 | 2675 | 260 | 85 | 43 |
| 5[c] | 155–300 | 2331 | 154 | 59 | 27 |
| 6[d] | 162–300 | 2416 | 221 | 70 | 34 |

[a]Cl[CF(CF$_3$)O(CF$_2$)$_4$OCF(CF$_3$)]$_d$Cl, where d is 5.6.
[b]CF$_3$O[CF$_2$CF(CF$_3$)O]$_p$(CF$_2$O)$_q$CF$_3$, where p is 58 and q is 2.
[c]Formula I where Z is Cl and (R$_f$)$_x$ is —CF$_2$CF$_2$—.
[d]Formula I where Z is H and (R$_f$)$_x$ is —CF$_2$CF$_2$—.
[e]Determined by end group analysis (F-nmr).

EXAMPLE 8

This example describes the preparation of a methyl carboxylate-terminated perfluoropolyether photopolymer.

A photopolymer (15.0 g) having the structure of formula I, where (R$_f$)$_x$ is —CF$_2$CF$_2$— and Z is COF, having a number average molecular weight of 3250, was treated with 15.0 g of a boron trifluoride-methanol complex, BF$_3$.2CH$_3$OH, and the mixture stirred at room temperature for 30 min. Water (50 ml) was added and the reaction mixture poured into a separatory funnel. The lower perfluoropolyether phase was dried over silica gel and filtered. The funnel was rinsed with Freon 113, and these rinsings added to the perfluoropolyether phase. The Freon was removed under reduced pressure to yield 14.8 g of liquid perfluoropolyether product having structure of formula I, where (R$_f$)$_x$ is —CF$_2$CF$_2$— and Z is —COOCH$_3$, as identified by H-nmr and infrared analyses.

EXAMPLE 9

This example describes the preparation of a methylol-terminated perfluoropolyether photopolymer.

Sodium borohydride (0.23 g) was slurried in 15 ml dimethoxyethane. Photopolymer (5 g) having the structure of formula I, where (R$_f$)$_x$ is —CF$_2$CF$_2$— and Z is COF, was added. A slight exotherm to 30° C. was observed. The reaction mixture was heated to 80° C. and stirred at this temperature for 5 hrs. Then 25 ml water and 25 ml of 10% aqueous sulfuric acid were added. Freon 113 (25 ml) was added and the fluorocarbon phase separated and the Freon removed under reduced pressure. The residual liquid product was then placed under a vacuum of 0.2 torr for 2 hours. A total 4.6 g of liquid perfluoropolyether product having the structure of formula I, where (R$_f$)$_x$ is —CF$_2$CF$_2$— and Z is —CH$_2$OH, was obtained as identified by H-nmr and infrared analyses. The glass transition temperature of the product (having a number average molecular weight of 3060) was found to be −44° C. by differential thermal analysis.

EXAMPLE 10

This example describes the preparation of N(2-hydroxyethyl) carboxamide-terminated perfluoropolyether photopolymer.

Aminoethanol (0.5 g) was dissolved in 15 ml dimethoxyethane in a 100 ml flask. Photopolymer (5.0 g) having the structure of formula I, where (R$_f$)$_x$ is —CF$_2$CF$_2$— and Z is COF, was dissolved in 10 ml of Freon 113 and the resulting solution added dropwise with stirring to the flask containing the aminoethanol. The reaction mixture was stirred for 2 hrs. at room temperature then 40 ml water was added and the mixture stirred for several additional minutes. The fluorocarbon phase was removed and dried over silica gel. The Freon was removed under reduced pressure to yield 5.8 g of liquid product. H-nmr and infrared analyses showed the presence of material having the structure of formula I, where (R$_f$)$_x$ is —CF$_2$CF$_2$— and Z is —CONHCHhd 2CH$_2$OH, and some chain-extended perfluoropolyether product containing the —PPE—CONHCH$_2$C-H$_2$OCO—PPE— structural unit.

EXAMPLE 11

This example describes the preparation of the acrylate of the methylol-terminated perfluoropolyether photopolymer. Methylol-terminated photopolymer of Example 9 (45 g) was dissolved in 50 ml Freon 113 and then 3.55 g dry triethylamine was added. Acryloyl chloride (3.3 g) dissolved in 50 ml Freon 113 was added over a 10-min. period. The reaction mixture was allowed to stir overnight at room temperature. At the end of the reaction period, 1.1 ml triethylamine and 1.2 ml of water were added. The reaction mixture was refluxed for 1 hr. then filtered through "Super Cel" diatomaceous earth filter aid. The filter cake was washed with 100 ml Freon 113 and the fluorocarbon phases combined. The resulting solution was acidified with anhydrous HCl and then filtered through "Super Cel". Freon 113 was removed under reduced pressure at ambient temperature. A total of 45.7 g of yellow oil was obtained. Infrared and H-nmr analyses of the oil were consistent with the structure of formula I, where Z is —CH$_2$OCOCH=CH$_2$ and (R$_f$)$_x$ is —CF$_2$CF$_2$—.

EXAMPLE 12

Following the procedure of Example 1, 18.8 g of perfluoro-N-propylamino-N,N-dipropionyl fluoride was dissolved in 60 ml diglyme containing 2.0 g dry cesium fluoride. To this stirred mixture was added 25.7 g of HFPO and the reaction mixture allowed to stir overnight with gradual warming to room temperature. The lower fluorocarbon was then removed and distilled at atmospheric pressure. A total of 16.0 g distilled between 45°–150° C., 7.5 g between 150°–190° C., and 11.4 g between 210°–230° C. F-nmr analysis of the two highest boiling fractions supported a product having a mixture of structures of formula I where in some structures $a+b=0$ and in others $a+b=1$ where $(R_f)_x$ is $-CF_2N(CF_2CF_2CF_3)CF_2-$ and Z is COF.

Various modifications and alterations of this invention will become apparent to those skilled in the art without departing from the scope and spirit of this invention.

I claim:

1. Perfluoropolyether substance comprising one or a mixture of polyether compounds each consisting essentially of 2 to 20 perfluoropolyether segments bonded together in a chain, each of which segments consist essentially of (1) at least one perfluoroisopropyleneoxy unit, (2) a bis(perfluoromethyleneoxy-terminated) unit of the formula $OCF_2(R_f)_xCF_2O$ where x is zero or 1 and $R_f$ is a fluoroaliphatic group, and (3) two perfluoroethylidene units terminating the ends of each said segment, the chain being terminated with $-COF$ or a moiety independently selected from the group consisting of H, X, $CF_2H$, $CF_2X$, $CH_2OH$, COX, COR, COOH, COOM, COOR, $CF_2R$, $CH_2OC(O)CR'=CH_2$, $CON(R'')R''$, $CH_2NH_2$, $CH_2NCO$, CN, $C_3N_3(R_f')_2$, $CH_2OCOR$, where X is F, Cl, or Br, M is an ammonium radical or a monovalent metal atom, R is alkyl, aryl, or a combination thereof, R' is H or $CH_3$, R'' is H, said R, $(CH_2)_zSi(R''')_3$ where z is 2 to 11 and R''' is a hydrolyzable group, or the two R'' groups can together form an alkylene moiety which together with the amido nitrogen atom form a heterocyclic ring, and $R_f'$ is a fluoroaliphatic radical.

2. Perfluoropolyether substance according to claim 1 wherein both ends of said chain are terminated with $-COF$.

3. Perfluoropolyether substance according to claim 1 wherein both ends of said chain are terminated with $CF_3F$, Cl, or H.

4. Normally liquid perfluoropolyether substance comprising one or a mixture of polyether compounds represented by the formula

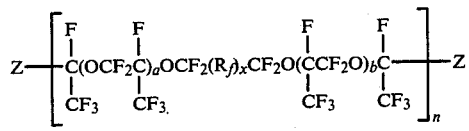

where $R_f$ is a fluoroaliphatic group, Z is $-COF$ or a moiety independently selected from the group consisting of H, X, $CF_2H$, $CF_2X$, $CH_2OH$, COX, COR, COOH, COOM, COOR, $CF_2R$, $CH_2OC(O)CR'=CH_2$, $CON(R'')R''$, $CH_2NH_2$, $CH_2NCO$, CN, $C_3N_3(R_f')_2$, $CH_2OCOR$, where X is F, Cl, or Br, M is an ammonium radical or a monovalent metal atom, R is alkyl, aryl, or a combination thereof, R' is H or $CH_3$, R'' is H, said R, $(CH_2)_zSi(R''')_3$ where z is 2 to 11 and R''' is a hydrolyzable group, or the two R'' groups can together form an alkylene moiety with 2 to 6 carbon atoms which together with the amido nitrogen atom form a heterocyclic ring, and $R_f'$ is a fluoroaliphatic radical, n is 2 to 20, x is zero or 1, and a and b are independently 0 to 10 with the proviso that the sum of $a+b$ is equal to at least 1.

5. The perfluoropolyether substance of claim 4 where both Z's are COF.

6. The perfluoropolyether substance of claim 4 where both Z's are $CH_2OH$.

7. The perfluoropolyether substance of claim 4 where both Z's are Cl.

8. The perfluoropolyether substance of claim 4 where both Z's are H.

* * * * *

UNITED STATES PATENT AND TRADEMARK OFFICE
CERTIFICATE OF CORRECTION

PATENT NO. :   4,647,413
DATED      :   March 3, 1987
INVENTOR(S) :  Patricia M. Savu It is certified that error appears in the above-identified patent and that said Letters Patent is hereby corrected as shown below:

Col. 2, lines 55-56, "independently (which can be zero) an integer" should read -- independently an integer (which can be zero) --

Col. 3, line 4, "$CH_2OCOR$" should read -- and $CH_2OCOR$ --

Col. 13, line 38, "$CH_2OCOR$" should read -- and $CH_2OCOR$ --

Col. 14, line 24, "$CH_2OCOR$" should read -- and $CH_2OCOR$ --

Col. 14, line 8, "$CF_3F$" should read -- $CF_3,F$ --

Signed and Sealed this

Ninth Day of May, 1989

*Attest:*

DONALD J. QUIGG

*Attesting Officer*   *Commissioner of Patents and Trademarks*